United States Patent [19]

Tanigaki

[11] Patent Number: 4,670,581

[45] Date of Patent: Jun. 2, 1987

[54] BIPHENYL COMPOUNDS AND PROCESS FOR PRODUCING THE SAME

[75] Inventor: Teiichi Tanigaki, Matsuyama, Japan

[73] Assignee: Sugai Chemical Industry Co., Ltd., Wakayama, Japan

[21] Appl. No.: 569,667

[22] Filed: Jan. 10, 1984

[30] Foreign Application Priority Data

| Jan. 27, 1983 | [JP] | Japan | 58-10489 |
| Sep. 9, 1983 | [JP] | Japan | 58-165216 |
| Sep. 9, 1983 | [JP] | Japan | 58-165217 |
| Nov. 22, 1983 | [JP] | Japan | 58-220422 |

[51] Int. Cl.$^4$ .......................................... C07C 69/76
[52] U.S. Cl. ........................... 560/108; 560/20; 560/53; 560/254; 560/255; 562/460; 562/463; 568/332; 568/333; 568/747
[58] Field of Search ............. 620/104; 560/20, 53, 560/254, 255, 108; 562/460, 463; 568/332, 333, 747

[56] References Cited

U.S. PATENT DOCUMENTS

| 4,065,489 | 12/1977 | Steinstrasser | 560/059 |
| 4,138,359 | 2/1979 | Mizukudi | 560/108 |
| 4,235,736 | 11/1980 | Beguin | 560/108 |
| 4,402,855 | 9/1983 | Zann et al. | 560/108 |
| 4,473,487 | 9/1984 | Romer et al. | 560/108 |
| 4,474,679 | 10/1984 | Dubois et al. | 560/108 |

FOREIGN PATENT DOCUMENTS

| 153-826A | 9/1985 | European Pat. Off. | 560/108 |
| 2719123 | 12/1977 | Fed. Rep. of Germany | 560/108 |
| 56-47642 | 4/1980 | Japan | 560/108 |

OTHER PUBLICATIONS

Dvolaitzky, et al, Tetrahedron 32 (14) 1835-8 1975.
Tetrahedron, vol. 32, pp. 1835–1838, 1978.

*Primary Examiner*—Paul J. Killos
*Attorney, Agent, or Firm*—Browdy and Neimark

[57] ABSTRACT

New biphenyl compounds and a process for producing them are provided. These new compounds have an acyloxy group in the 2- or 4-position of the biphenyl and an acyl hydroxyalkyl, hydroxyalkenyl or vinyl group in the 4'-position of the biphenyl or, alternatively a hydroxyl group in the 2- or 4-position of the biphenyl and an acyl, hydroxyalkyl, hydroxyalkenyl or vinyl group in the 4'-position of the biphenyl. These compounds can be produced easily from 2- or 4-acyloxybiphenyl compounds.

21 Claims, No Drawings

BIPHENYL COMPOUNDS AND PROCESS FOR PRODUCING THE SAME

BACKGROUND OF THE INVENTION

The present invention relates to new biphenyl compounds and a process for producing them. More particularly, the invention relates to new biphenyl compounds of which two phenyl groups are substituted by different functional groups having a high reactivity and a process for producing them.

It has been known that polymers having biphenyl groups have excellent heat and chemical resistance.

To introduce the biphenyl group into a polymer, it is necessary to prepare a biphenyl compound having highly reactive functional groups introduced into the two phenyl groups.

The biphenyl compounds having these functional groups are valuable not only as starting materials for polymers but also as intermediates in the synthesis of medicines, agricultural chemicals and dyes.

Under these circumstances, the present inventors have investigated biphenyl compounds having an active functional group in each of the phenyl groups, and as a result thereof, found new compounds and a process for producing them.

OBJECTS OF THE INVENTION

A first object of the present invention is to provide new biphenyl compounds having an acyloxy group in the 2- or 4-position and an acyl, hydroxyalkyl, hydroxyalkenyl or vinyl group in the 4'-position and a process for producing them.

A second object of the invention is to provide new biphenyl compounds having a hydroxyl group in the 2- or 4-position and an acyl, hydroxyalkyl, hydroxyalkenyl or vinyl group in the 4'-position and a process for producing them.

A third object of the present invention is to provide new biphenyl compounds having different, highly reactive groups in the 2- or 4-position and 4'-position and suitable for use as starting materials for polymers or intermediates for the synthesis of medicines, agricultural chemicals or dyes.

DESCRIPTION OF THE PREFERRED EMBODIMENTS

The compounds of the present invention will be classified into the following groups and the invention will be described according to this classification:

Compound group A:

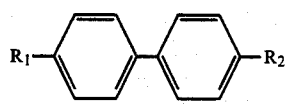

wherein $R_1$ is an acyloxy group and $R_2$ is an acyl, 1-hydroxyalkyl or vinyl group or, alternatively, $R_1$ is a hydroxyl group and $R_2$ is a 1-hydroxyalkyl group or vinyl group, Compound group B:

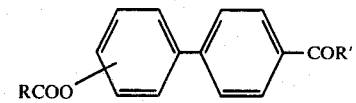

wherein R and R' are each a lower alkyl group and the RCOO group is situated in the 2- or 4-position, Compound group C:

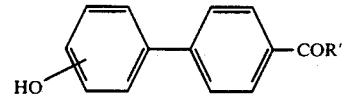

wherein R' has the same meaning as above and the HO group is situated in the 2- or 4-position, and Compound group D:

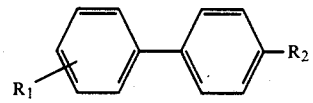

wherein $R_1$ is situated in the 2- or 4-position and is a hydroxyl group and $R_2$ is a 1-hydroxy-1-methylalkyl or 1-hydroxyl-1-methylalkenyl group or, alternatively, $R_1$ is an acetoxy group and $R_2$ is a 1-hydroxyl-1-methylalkenyl group.

Compound group A: This group includes the following new biphenyl compounds (1) to (5):

4-acetoxy-4'-acetylbiphenyl (1)

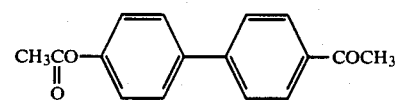

4-acetoxy-4'-(1-hydroxyethyl)biphenyl (2)

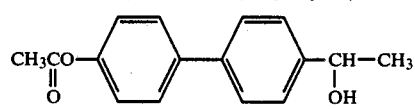

4-acetoxy-4'-vinylbiphenyl (3)

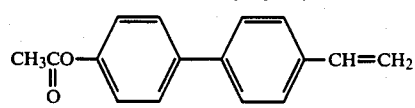

4-hydroxy-4'-(1-hydroxyethyl)biphenyl (4)

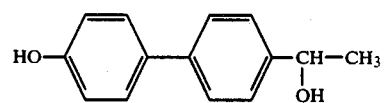

4-hydroxy-4'-vinylbiphenyl (5)

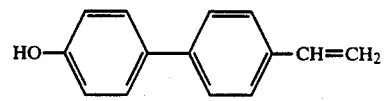

These compounds are produced generally by the following processes: a 4-acyloxy-4'-acylbiphenyl of the following general formula (I) obtained by Friedel-Crafts reaction of a 4-acyloxybiphenyl of the following general formula (P) is reduced to obtain a 4-acyloxy-4'-

(1-hydroxyalkyl)biphenyl of the following general formula (II) or 4-hydroxy-4'-(1-hydroxyalkyl)biphenyl of the following formula (IV). When the compound (IV) is acylated, the compound (II) is obtained. When the compound (IV) is dehydrated, a 4-hydroxy-4'-(1-alkenyl)-biphenyl of the following formula (V) is obtained. When the compound (V) is acylated, a 4-acyloxy-4'-(1-alkenyl)biphenyl of the following general formula (III) is obtained. The compounds (III) may be obtained also by the dehydration of the compound (II). The compound of the general formula (I) may be obtained by acylating a 4-hydroxy-4'-acylbiphenyl of the following general formula (Q) obtained by Fries rearrangement of the 4-acyloxy-biphenyl (P).

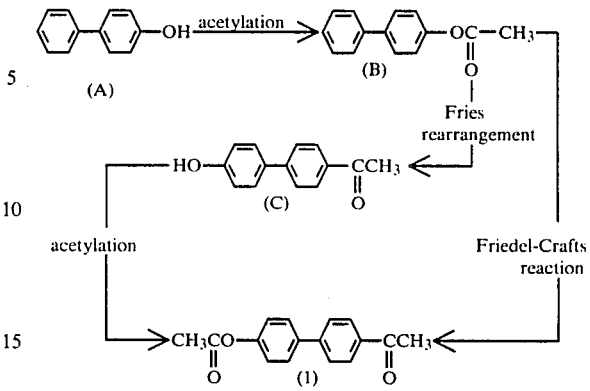

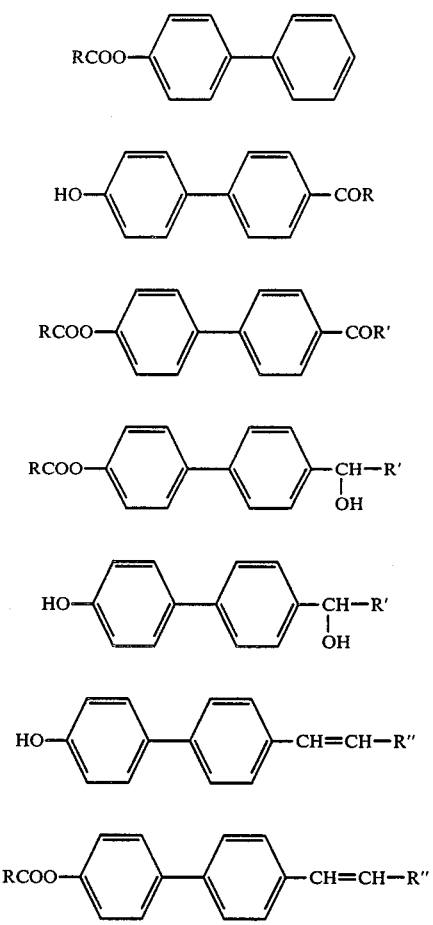

wherein R and R' have the same meaning as above and R" is a lower alkyl group having a carbon number smaller than that of R' by one, or a hydrogen atom.

These processes will be illustrated with reference to the new biphenyl compounds (1) to (5). The new biphenyl compound (1) is produced by acetylating 4-hydroxybiphenyl(A) to obtain 4-acetoxybiphenyl(B) and then reacting the compound (B) with an acyl halide of the general formula (VII) given below or an acid anhydride in the presence of a Friedel-Crafts catalyst in a solvent as shown in the following reaction formula:

The Friedel-Crafts catalysts include, for example, $AlCl_3$, $FeCl_3$, $TiCl_4$, $SnCl_4$, $ZnCl_2$ and $BF_3O(C_2H_5)_2$. Among them, $AlCl_3$ and $FeCl_3$ are preferred from the viewpoint of the yield of the compound (1) and $AlCl_3$ is particularly preferred. The solvents include, for example, halogenated lower aliphatic hydrocarbons such as $CH_2Cl_2$, $CHCl_3$ and $CCl_4$ as well as $CS_2$ and nitrobenzene.

The above-mentioned Friedel-Crafts catalyst is added to the solvent, the acyl halide of the following general formula (VII) or an acid anhydride of the following general formula (R) is added thereto under stirring to obtain a solution and the solution is stirred at a temperature in the range of room temperature to a reflux temperature of the solvent (under reflux) for 5 to 100 h to complete the reaction.

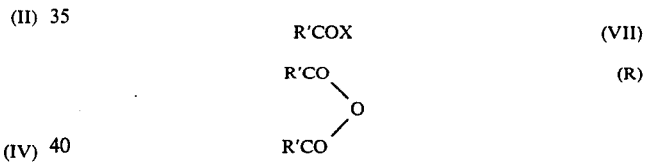

Then, the reaction mixture is thrown into ice/water to separate the solvent layer, which is then concentrated to obtain the new biphenyl compound (1).

The molar ratio of the acyl halide or acid anhydride to the compound (B) is in the range of 1:1.2 to 1:2.0. The molar ratio of the Friedel-Crafts catalyst to the compound (B) is 1:2 to 1:5.

The new biphenyl compound (1) may be produced also by subjecting the compound (B) to the Fries rearrangement in the presence of $AlCl_3$ or $ZnCl_2$ as a catalyst in nitrobenzene or in the presence of $AlC_3$—NaCl as a catalyst without using any solvent to obtain 4-hydroxy-4'-acetylbiphenyl (C) and then acetylating the compound (C) with acetic anhydride.

When the new biphenyl compound (1) or the above-mentioned 4-hydroxy-4'-acetylbiphenyl (C) is reduced, the new biphenyl compound (4) of the present invention is obtained.

In carrying out the reduction, there may be employed a process wherein the compound is reduced with hydrogen in the presence of a catalyst containing a platinum group metal such as Rh or Pt or a transition metal such as Fe, Co or Ni or a process wherein a metal hydride such as sodium borohydride or lithium aluminum hydride is used.

When the thus obtained new biphenyl compound (4) is acetylated with, for example, acetic anhydride, the new biphenyl compound (2) of the present invention is obtained.

When the new biphenyl compound (1) is reduced in the presence of sodium borohydride under given reduction conditions, the new biphenyl compound (2) is obtained directly:

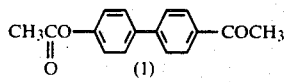

expected taking advantage of the reactivity difference. When the new biphenyl compound (4) is dehydrated, the new biphenyl compound (5) of the present invention is obtained. When the compound (5) is acetylated, the new biphenyl compound (3) of the present invention is obtained.

When the new biphenyl compound (2) is dehydrated, a mixture of the new biphenyl compounds (5) and (3) in nearly equivalent amounts is obtained. When the mixture is hydrolyzed, the compound (5) is obtained.

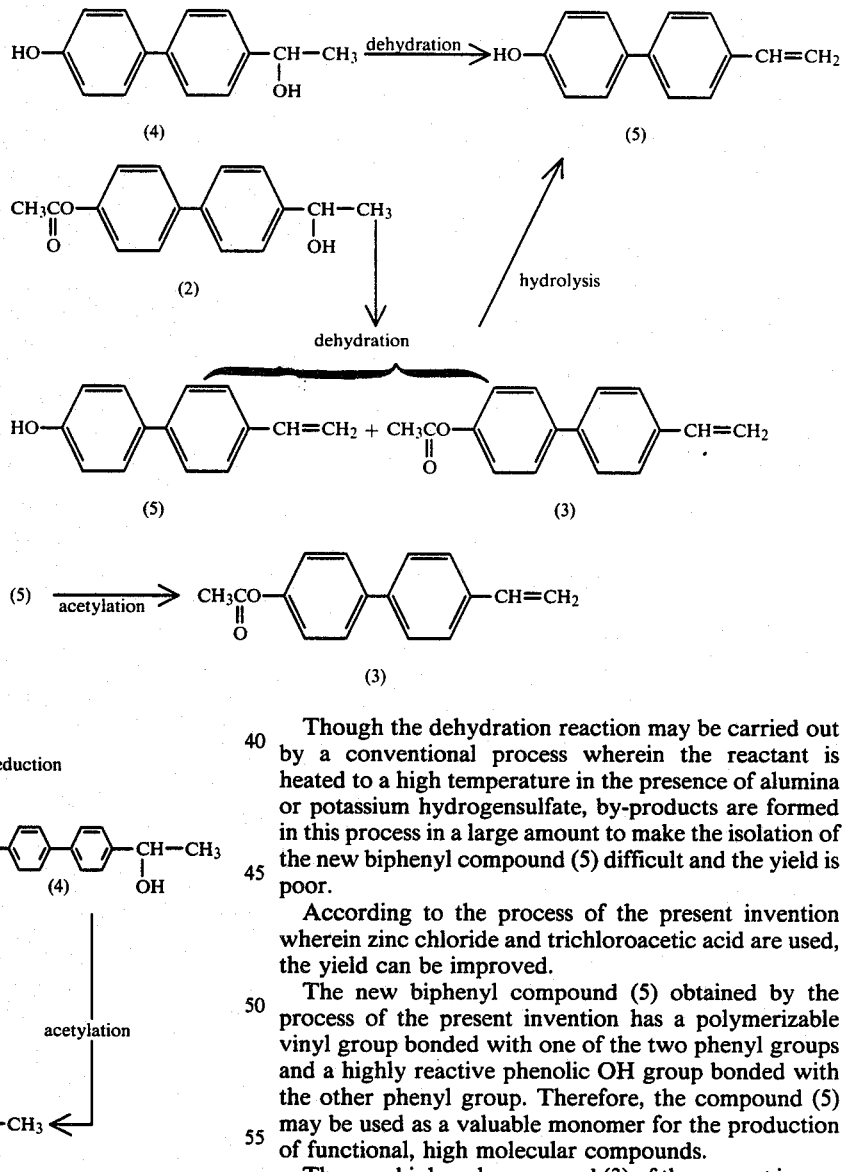

The resulting new biphenyl compound (4) has a phenolic OH group and an alcoholic OH group in the two phenyl groups, respectively. The compound (2) has two functional groups having different reactivities, i.e. an alcoholic OH group and acetoxy group in the two phenyl groups, respectively. The use of these compounds as an intermediate for the production of polymers having high thermal and chemical resistance, or as intermediates for new agricultural chemicals and dyes is Though the dehydration reaction may be carried out by a conventional process wherein the reactant is heated to a high temperature in the presence of alumina or potassium hydrogensulfate, by-products are formed in this process in a large amount to make the isolation of the new biphenyl compound (5) difficult and the yield is poor.

According to the process of the present invention wherein zinc chloride and trichloroacetic acid are used, the yield can be improved.

The new biphenyl compound (5) obtained by the process of the present invention has a polymerizable vinyl group bonded with one of the two phenyl groups and a highly reactive phenolic OH group bonded with the other phenyl group. Therefore, the compound (5) may be used as a valuable monomer for the production of functional, high molecular compounds.

The new biphenyl compound (3) of the present invention having the acetoxy group bonded with one of the two phenyl groups has a polymerization reactivity higher than that of the compound (5). The compound (3) may be used broadly for the production of functional, high molecular compounds like the compound (5).

Compound group B: This group includes new biphenyl compounds shown below:

4-benzoyloxy-4'-benzoylbiphenyl (11)   4-acetoxy-4'-(3-carboxy)propionylbiphenyl (12)

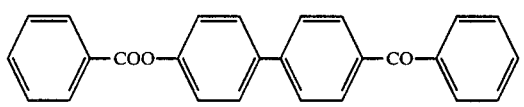

4-acetoxy-4'-n-decanoylbiphenyl (13)

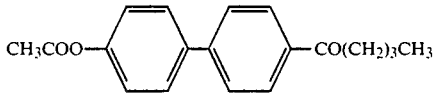

4-acetoxy-4'-(5-ethoxycarbonylvaleryl)biphenyl (15)

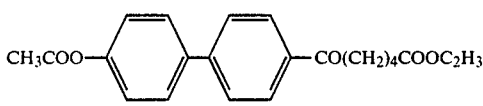

4-acetoxy-4'-(p-acetoxy-m-bromobenzoyl)biphenyl (17)

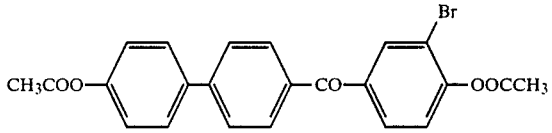

4-acetoxy-4'-(3-hydroxy-2-naphthoyl)biphenyl (19)

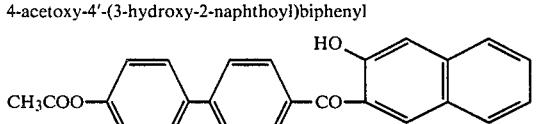

4-(p-nitrobenzoyloxy)-4'-p-nitrobenzoylbiphenyl (20)

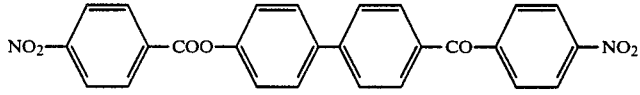

4-(p-acetoxybenzoyloxy)-4'-(p-acetoxybenzoyl)biphenyl (21)

di(4'-acetoxy-4-biphenylyl)diketone (22)

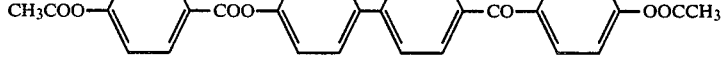

4-acetoxy-4'-(p-acetoxybiphenyl-p'-carbonylvaleryl)biphenyl (23)

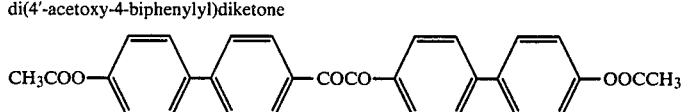

4-methacryloyl-4'-benzoylbiphenyl (24)

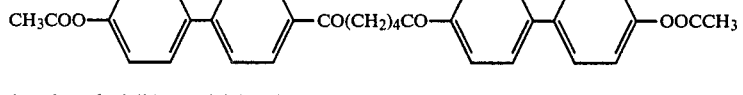

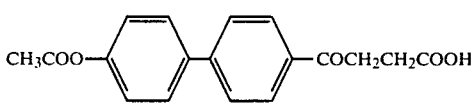

4-acetoxy-4'-(p-methoxycarbonylbenzoyl)biphenyl (14)

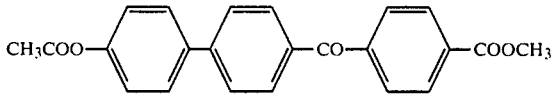

4-acetoxy-4'-chloroacetylbiphenyl (16)

4-acetoxy-4'-methacryloylbiphenyl (18)

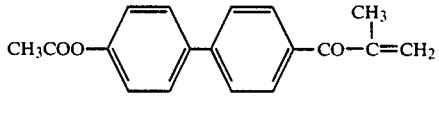

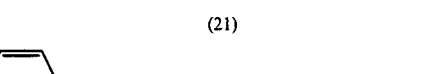

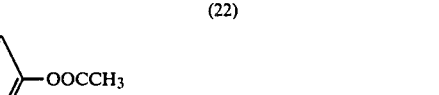

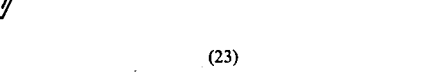

4-acetoxy-4'-benzoylbiphenyl (25)

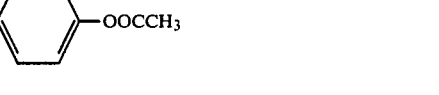

These compounds are produced generally by the following processes: a 2- or 4-acyloxybiphenyl of the following general formula (VI) is reacted with an acyl halide of the following general formula (VII) or an acid anhydride of the general formula (R) in the presence of a Friedel-Crafts catalyst in an inert solvent to obtain a 2- or 4-acyloxy-4'-acylbiphenyl of the following general formula (VIII)

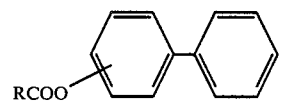 (VI)

R'COX (VII)

$$\begin{matrix} R'CO \\ \phantom{R'CO}\searrow O \\ R'CO \nearrow \end{matrix} \quad (R)$$

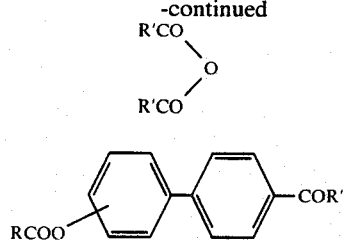 (VIII)

wherein R is a substituted or unsubstituted alkyl group, a substituted or unsubstituted alkenyl group or a substituted or unsubstituted aryl group, R' is substituted or unsubstituted alkyl group, a substituted or unsubstituted alkenyl group, a substituted or unsubstituted aryl group or a carbonyl halide group and X is a halogen atom.

The compounds of the general formula (VI) include various biphenyl carboxylates shown in the following Table 1. The symbol "R" in the formula represents a substituted or unsubstituted alkyl group, a substituted or unsubstituted alkenyl group or a substituted or unsubstituted aryl group. The substituents in the substituted alkyl, alkenyl or aryl group may be each a halogen atom or a nitro group. Preferably, R is a substituted or unsubstituted $C_1$ to $C_5$ alkyl group, a substituted or unsubstituted $C_1$ to $C_5$ alkenyl group or a substituted or unsubstituted phenyl or naphthyl group.

TABLE 1

[Structures of compound (VI) RCOO-biphenyl with R = $CH_3-$, $C_2H_5-$, $ClCH_2-$, $CH_2=CCH_3-$, phenyl, $NO_2$-phenyl, naphthyl, and corresponding biphenyl ester compounds.]

These biphenyl esters may be obtained easily by reacting a corresponding carboxylic acid RCOOH with 4-hydroxybiphenyl or by acylating the hydroxyl group of a corresponding 2- or 4-hydroxybiphenyl.

The acylated compound obtained by acylating the hydroxyl group of 2- or 4-hydroxybiphenyl may be used directly for the production of the group B compounds without separating the same from the reaction system.

The acyl halides of the general formula (VII) include, for example, compounds shown in Table 2. The symbol R' in the formula represents a substituted or unsubstituted alkyl group, a substituted or unsubstituted alkenyl group, a substituted or unsubstituted aryl group or a carbonyl halide group and X represents a halogen atom.

The substituents in the substituted alkyl, alkenyl and aryl groups include halogen atoms, and carboxyalkyl, chlorocarbonyl, acyloxy, hydroxyl, and nitro groups. Preferably, R' is a substituted or unsubstituted $C_1$ to $C_5$ alkyl group, a substituted or unsubstituted $C_1$ to $C_5$ alkenyl group, a substituted or unsubstituted phenyl or naphthyl group.

These acyl halides may be obtained easily by, for example, reacting a corresponding carboxylic acid with thionyl chloride, $PCl_3$ or $PCl_5$.

TABLE 2

| R' | R'COX (VII) Compound (VII) |
|---|---|
| $CH_3-$ | $CH_3COCl$ |
| $CH_3(CH_2)_8-$ | $CH_3(CH_2)_8COCl$ |
| $ClCH_3-$ | $ClCH_2COCl$ |
| $CH_2=CCH_3-$ | $CH_2=CCH_3COCl$ |
| $CH_3OOC-CH_2CH_2-$ | $CH_3OOC-CH_2-CH_2COCl$ |
| $C_2H_5OOC-(CH_2)_4-$ | $C_2H_5OOC-(CH_2)_4COCl$ |
| $ClCH_2-$ | $ClCH_2COCl$ |
| $ClCO-$ | $ClCOCOCl$ |
| $ClCO(CH_2)_4$ | $ClCO(CH_2)_4COCl$ |
| phenyl | phenyl-COCl |
| Cl-phenyl | Cl-phenyl-COCl |
| $CH_3COO$-phenyl | $CH_3COO$-phenyl-COCl |
| Br-, $CH_3COO$-phenyl | Br-, $CH_3COO$-phenyl-COCl |
| OH-naphthyl | OH-naphthyl-COCl |
| $NO_2$-phenyl | $NO_2$-phenyl-COCl |
| $CH_3COO$-phenyl | $CH_3COO$-phenyl-COCl |
| $OOCCH_3$-naphthyl | $OOCCH_3$-naphthyl-COCl |

The acid anhydrides of the general formula (R) used for the production of the group B compounds include aliphatic and aromatic carboxylic anhydrides. They include, for example, the following compounds:

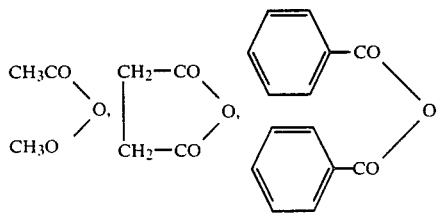

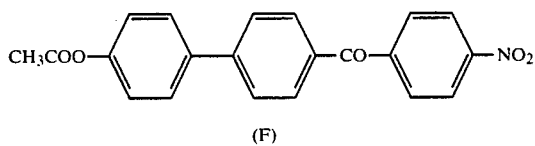

(F)

but the compound (G) is obtained according to the following reaction formula:

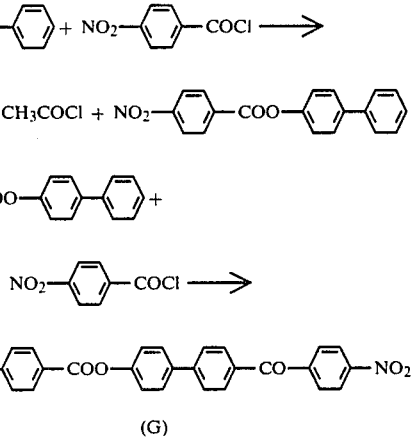

(G)

The Friedel-Crafts catalysts, reaction solvents, reaction temperature, reaction time, acyl halide or acid anhydride and the amount of the Friedel-Crafts catalyst used in the production of the group B compounds may be the same as those described above with reference to the production of the group A compounds.

It is to be noted that an acyl exchange reaction occurs under some reaction conditions in the process of the present invention.

When the molar ratio of benzoyl chloride to 4-acetoxybiphenyl is 1:1.2, compound (D) [compound (25)] is obtained as will be shown in Example 12 given below according to the following reaction formula:

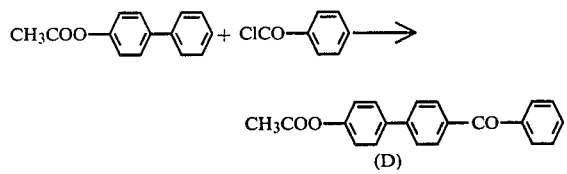

(D)

However, when the molar ratio is altered to 1:2.0, the following acyl exhange reaction occurs to form compound (E) [compound (11)].

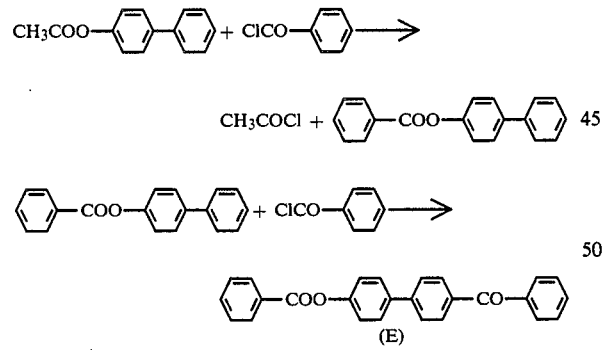

(E)

In the production of the compound (20), the following compound (F) can not be obtained:

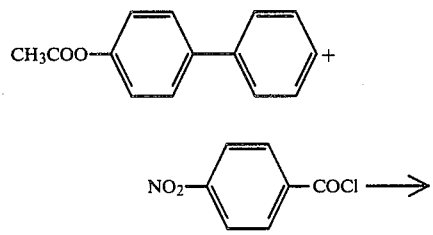

Such an exchange reaction occurs also in the production of the compound (21).

Compound group C: This group includes new biphenyl compounds shown below:

4-hydroxy-4'-benzoylbiphenyl (31)

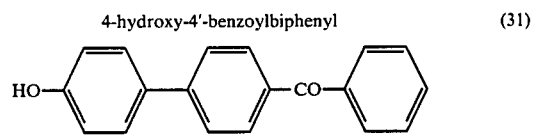

4-hydroxy-4'-p-chlorobenzoylbiphenyl (32)

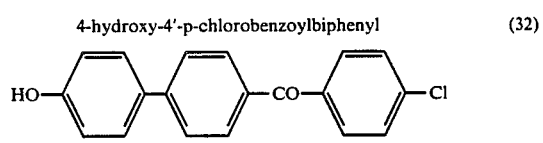

4-hydroxy-4'-(3-carboxypropionyl)biphenyl (33)

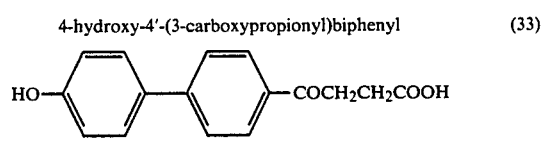

4-hydroxy-4'-n-decanoylbiphenyl (34)

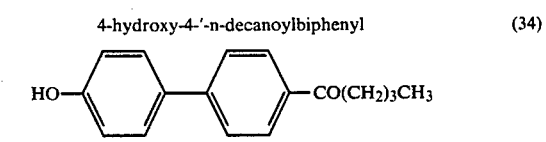

4-hydroxy-4'-(p-carboxybenzoyl)biphenyl (35)

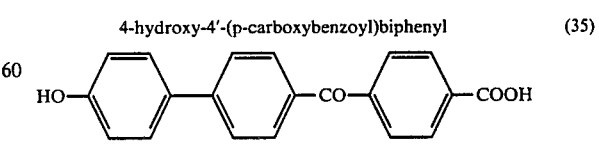

4-hydroxy-4'-(5-carboxyvaleryl)biphenyl (36)

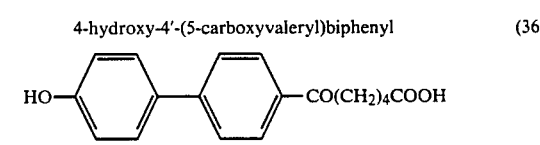

-continued 4-hydroxy-4'-(p-hydroxybenzoyl)biphenyl (37)

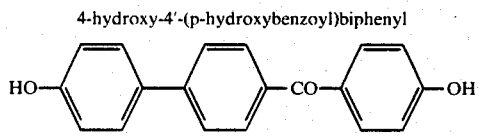

These compounds are produced by the following processes: a 2- or 4-acyloxybiphenyl of the following general formula (VI) is reacted with an acyl halide of the following general formula (VII) or an acid anhydride of the following general formula (R) in the presence of a Friedel-Crafts catalyst in an inert solvent and then the resulting 2- or 4-acyloxy-substituted 4'-acyl-biphenyl of the following general formula (VIII) is hydrolyzed to obtain a 2- or 4-hydroxy-4'-acylbiphenyl of the general formula (IX):

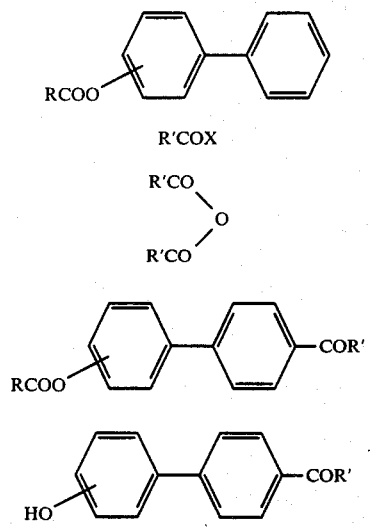

wherein R is a substituted or unsubstituted alkyl group, a substituted or unsubstituted alkenyl group or a substituted or unsubstituted aryl group, R' is a substituted or unsubstituted alkyl group, a substituted or unsubstituted alkenyl group, a substituted or unsubstituted aryl group or a carbonyl halide group and X is a halogen atom.

The production conditions for the compounds of the general formulae (VI) and (VII), the acid anhydride (R) and the compounds of the general formula (VIII) and the acyl exchange reaction are the same as those described above with reference to the group B compounds.

The compounds of the general formula (IX) may be produced easily by hydrolyzing the compound of the general formula (VIII) preferably in the presence of an alkali.

As the solvent for the hydrolysis reaction, water or tetrahydrofuran is used. NaOH is used as the alkali. Generally, the reaction is carried out under heating and reflux of the solvent.

The compounds of groups B and C may be used as starting materials for polymers or intermediates in the synthesis of medicines, agricultural chemicals and dyes, taking advantage of the highly reactive groups in the 2- or 4-position and in the 4'-position.

Compound group D: This group includes new biphenyl compounds shown below:

4-hydroxy-4'-(1-hydroxyisopropyl)biphenyl (51)

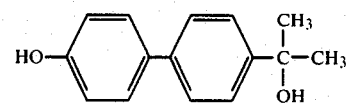

4-hydroxy-4'-isopropenylbiphenyl (52)

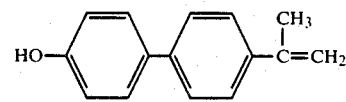

4-acetoxy-4'-isopropenylbiphenyl (53)

These compounds are prepared in the same manner as described above with reference to the group A compounds as follows: 2- or 4-hydroxybiphenyl (A') is acylated to obtain a 2- or 4-acyloxybiphenyl (VI), which is then subjected to the Friedel-Crafts reaction or Fries rearrangement followed by acetylation to obtain a 2- or 4-acyloxy-4'-acylbiphenyl compound (VIII). The compound (VIII) is reacted with magnesium and a methyl halide according to a Grignard reaction to obtain a 2- or 4-hydroxy-4'-(1-hydroxy-1-methylalkyl)biphenyl (X). The compound (X) is dehydrated to obtain a 2- or 4-hydroxy-4'-(1-methylalkenyl)biphenyl (XI), which is acylated to obtain a 2- or 4-acyloxy-4'-(1-methylalkenyl)biphenyl:

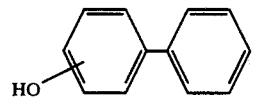 (A')

 (VI)

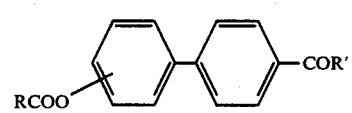 (VIII)

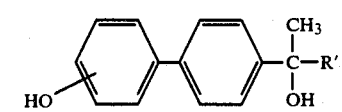 (X)

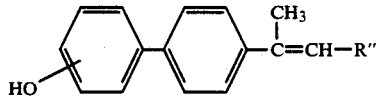 (XI)

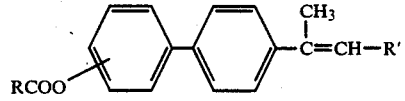 (XII)

wherein R and R' are each a substituted or unsubstituted alkyl group and R' is a substituted or unsubstituted alkyl group having a carbon number smaller than that of R' by one, or a hydrogen atom.

When 4-hydroxybiphenyl is used as the compound (A'), the reaction proceeds as follows:

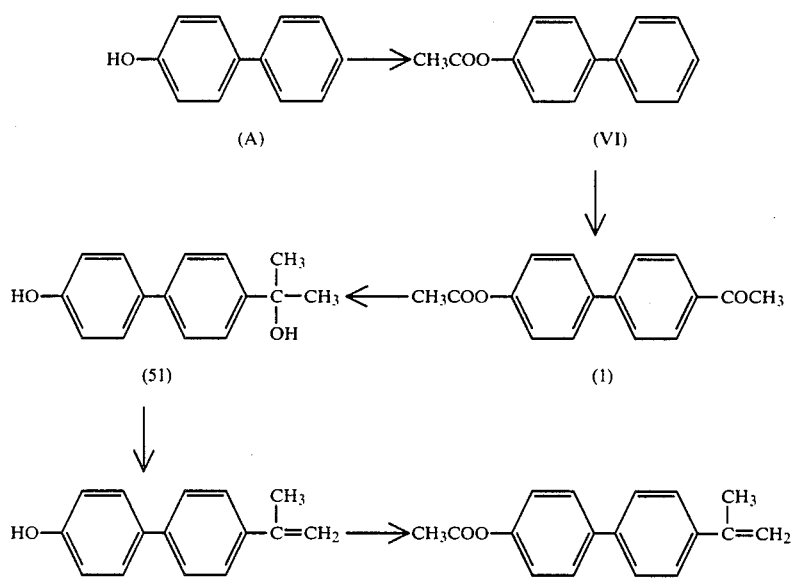

The Friedel-Crafts reaction and Fries rearrangement are carried out in the same manner as in the reaction of the group A compounds.

In a conventional dehydration process, the compound is heated to a high temperature in the presence of alumina or potassium hydrogensulfate. However, in this process, by-products are formed in a large amount and the new biphenyl compound (52) cannot be isolated easily and the yield is poor.

According to the process of the present invention wherein zinc chloride and trichloroacetic acid are used, the yield can be increased.

Further, the new biphenyl compound (53) is obtained by reacting the new biphenyl compound (52) with acetic anhydride.

The thus obtained new biphenyl compound (51) has functional groups having different reactivities such as the phenolic OH group and alcoholic OH group. The use of this compound as a starting material for polymers having high resistance to heat and chemicals or as an intermediate for new agricultural chemicals and dyes is expected taking advantage of the difference in reactivity.

The new biphenyl compounds (52) and (53) having a polymerizable isopropenyl group bonded with one of the two phenyl groups and a highly reactive phenolic OH or acetoxyl group bonded with the other phenyl group may be used as monomers useful particularly for the production of highly functional high-molecular compounds.

The following examples will further illustrate the present invention:

EXAMPLE 1

Production of 4-hydroxy-4'-acetylbiphenyl (C) (Fries rearrangement)

A mixture of 10 g of aluminum chloride and 2 g of common salt was placed in flask provided with a calcium chloride drying tube and then heated to 180° C. to fuse aluminum chloride. A homogeneous liquid thus obtained was cooled to 140° C. 5 g of biphenyl acetate (B) having a melting point of 81.0° to 82.0° C. was added thereto and the mixture was heated again to 180° C. for 3 min.

The reaction mixture was cooled to room temperature and poured into ice/water containing hydrochloric acid. 30 ml of methylene chloride was added thereto and the resulting mixture was stirred.

A methylene chloride layer was separated, washed with water and dried. Hexane was added thereto in portions and a resulting yellowish brown oil was separated out. The remaining solution was concentrated to obtain a solid, which was recrystallized from a solvent mixture of acetone and hexane to obtain 4-hydroxy-4'-acetylbiphenyl (C) in the form of white crystals:

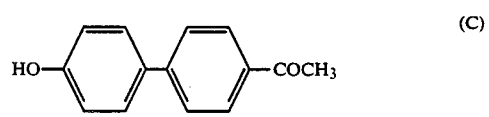

Yield: 0.7 g

Melting point: 207.5° to 208.5° C.

Characteristic infrared absorption: OH structure: 3300 cm$^{-1}$. C=O structure: 1650 cm$^{-1}$.

It was confirmed according to a liquid chromatography that the product comprises a single compound.

EXAMPLE 2

Production of 4-acetoxy-4'-acetylbiphenyl (1)

10.5 g of 4-hydroxy-4'-acetylbiphenyl (C) obtained in Example 1 was heated together with 20 ml of acetic anhydride in the presence of a small amount of concentrated sulfuric acid. Crude crystals thus obtained were recrystallized from carbon tetrachloride to obtain 12.5 g of 4-acetoxy-4'-acetylbiphenyl (1):

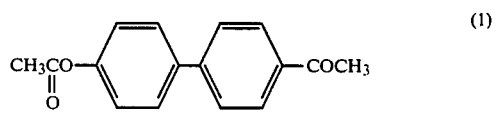

Yield: 97%

Melting point: 124.5° to 126.5° C.

| Elementary analysis: | C (%) | H (%) |
|---|---|---|
| calculated: | 75.57 | 5.55 |
| found: | 75.76 | 5.57 |

Characteristic infrared absorption: $CH_3CO-$ structure: 1670 cm$^{-1}$. $CH_3COO-$ structure: 1750 cm$^{-1}$.
NMR parameter ($C^{13}$, in CDCl$_3$)

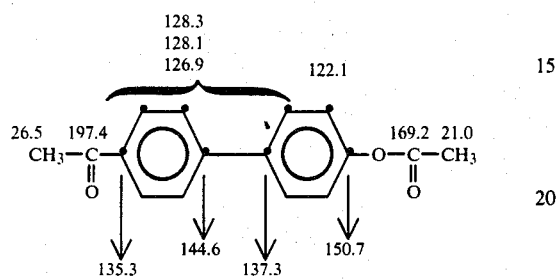

EXAMPLE 3

Production of 4-hydroxy-4'-(1-hydroxyethyl)biphenyl (4)

300 ml of methanol and 16.7 g of 4-acetoxy-4'-acetylbiphenyl (1) obtained in Example 2 were charged in a flask provided with a reflux condenser and a stirrer. 25 g of sodium borohydride was added thereto in portions under stirring at room temperature.

When lithium sodium hydride was added thereto, hydrogen bubbles were formed and the reaction solution was colored into yellow.

After completion of the addition of sodium borohydride, the stirring was continued for 30 min to complete the reaction.

The reaction solution was concentrated and the residue was thrown into water.

A yellowish white precipitate thus formed was separated and recrystallized from ethyl acetate to obtain 11.9 g of 4-hydroxy-4'-(1-hydroxyethyl)biphenyl (4) as white crystals:

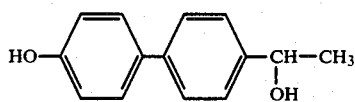

(4)

Yield: 85%
Melting point: 145° to 146° C.

The compound (4) was soluble in methanol, ethanol, acetone, tetrahydrofuran and ethyl acetate, difficultly soluble in benzene and chloroform and insoluble in hexane and ligroin.

| Elementary analysis: | C (%) | H (%) |
|---|---|---|
| calculated: | 78.48 | 6.59 |
| found: | 78.09 | 6.63 |

Characteristic infrared absorption:

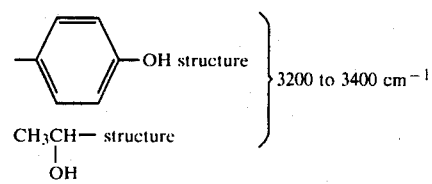

NMR parameter ($C^{13}$, in CDCl$_3$)

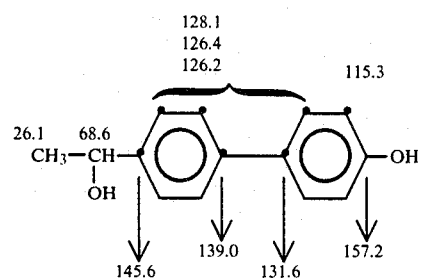

EXAMPLE 4

Production of 4-hydroxy-4'-(1-hydroxyethyl)biphenyl (4)

15 g of 4-hydroxy-4'-acetylbiphenyl (C) obtained in Example 1 was dissolved in 300 ml of tetrahydrofuran. 3 g of lithium aluminum hydride was added thereto in portions under stirring at room temperature.

Then, the same treatment as in Example 3 was effected to obtain 8.1 g of 4-hydroxy-4'-(1-hydroxyethyl)biphenyl (4) in the form of white crystals.

Yield; 53%.

The melting point, solubilities in the solvents, characteristic infrared absorption and NMR parameter were the same as those of Example 3.

EXAMPLE 5

Production of 4-acetoxy-4'-(1-hydroxyethyl)biphenyl (2)

10 g of 4-hydroxy-4'-(1-hydroxyethyl)biphenyl (4) obtained in Example 3 was dissolved in 20 ml of acetic anhydride. A small amount of concentrated sulfuric acid was added to the solution. The mixture was heated to 100° C. to obtain 4-acetoxy-4'-(1-hydroxyethyl)biphenyl (2) quantitatively:

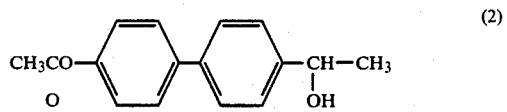

(2)

The product was recrystallized from an acetone/hexane solvent mixture.
Melting point: 142° to 143.5° C.

| Elementary analysis: | C (%) | H (%) |
|---|---|---|
| calculated: | 74.98 | 6.29 |
| found: | 74.35 | 6.20 |

Characteristic infrared absorption: C—O structure: 1670 cm$^{-1}$. HO structure: 3200 to 3400 cm$^{-1}$.
NMR parameter ($C^{13}$, in CDCl$_3$)

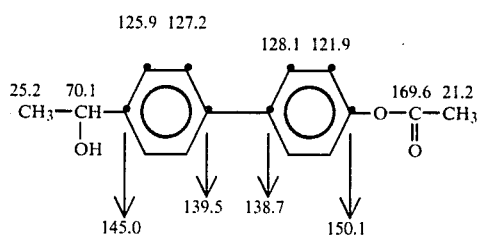

EXAMPLE 6

Production of 4-acetoxy-4'-(1-hydroxyethyl)biphenyl (2)

4-Acetoxy-4'-acetylbiphenyl (1) obtained in Example 2 was dissolved in dimethylformamide. Sodium borohydride in an equimolar amount as (1) was added thereto under stirring and the reaction was effected at about 5° C. for 5 hr.

Then, the same treatment as in Example 3 was effected to obtain 4-acetoxy-4'-(1-hydroxyethyl)biphenyl (2) in the form of white crystals. Yield: 70%.

The melting point, solubilities in the solvents, characteristic infrared absorption and NMR parameter were the same as those of Example 5.

The same procedure as above was repeated except that the molar number of sodium borohydride, solvent, reaction temperature and reaction time were altered to obtain the results shown in Table 3.

TABLE 3

| Molar ratio of reducing agent to compound (1) | Reducing agent | Solvent | Reaction temp. (°C.) | Reaction time | Yield of compound (2) (%) |
|---|---|---|---|---|---|
| 1.2 | NaBH₄ | MeOH—THF | room temp. | 15 min | 40 |
| 1.2 | NaBH₄ | MeOH | 5 | 30 min | 87 |
| " | " | MeOH | 5 | 2.5 hr | 76 |
| 1 | NaBH₄ | MeOH | 5 | 40 min | 70 |
| 0.5 | NaBH₄ | MeOH | 5 | 3 hr | 73 |

Notes:
MeOH: methanol
THF: tetrahydrofuran

EXAMPLE 7

Production of 4-hydroxy-4'-vinylbiphenyl (5)

150 ml of dimethyl sulfoxide and 50 g of 4-hydroxy-4'-(1-hydroxyethyl)biphenyl (4) obtained in Example 4 were charged in a flask provided with a condenser and a stirrer to obtain a homogeneous solution. 10 g of zinc chloride was added to the solution and the mixture was heated to 180° C. to dissolve zinc chloride. The reaction liquid was thus colored into yellow.

Then, 10 g of trichloroacetic acid was added thereto under stirring. The stirring was continued at 180° C. for 3 min.

The reaction solution was cooled to room temperature and poured into water. 40 g of a solid thus obtained was separated.

According to a liquid chromatographic analysis, the solid contained 32.9 g of 4-hydroxy-4'-vinylbiphenyl (5).

Yield: 72%.

The solid was recrystallized from a solution comprising a mixture of acetone and hexane and then from benzene to obtain 18.2 g of white crystals.

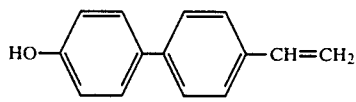

Yield: 40%
Melting point: 190° to 191.5° C.

It was confirmed according to the liquid chromatography that the product was a single compound.

| Elementary analysis: | C (%) | H (%) |
|---|---|---|
| calculated: | 85.68 | 6.16 |
| found: | 85.79 | 6.03 |

Characteristic infrared absorption: HO structure: 3350 cm⁻¹. —CH=CH₂ structure: 1620 cm⁻¹.

NMR parameter (in DMSO)

4-Hydroxy-4'-vinylbiphenyl (5) was easily soluble in methanol, ethanol, acetone, tetrahydrofuran and ethyl acetate, soluble in benzene and chloroform and insoluble in hexane and ligroin.

EXAMPLE 8

Production of 4-acetoxy-4'-vinylbiphenyl (3)

10 g of 4-hydroxy-4'-vinylbiphenyl (5) obtained in Example 7 was heated to 100° C. together with a small amount of concentrated sulfuric acid in 20 ml of acetic anhydride to obtain 4-acetoxy-4'-vinylbiphenyl (3) nearly quantitatively.

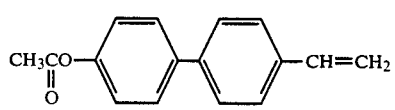

Melting point: 119° to 121.5° C.

| Elementary analysis: | C (%) | H (%) |
|---|---|---|
| calculated: | 80.64 | 5.92 |
| found: | 80.67 | 6.28 |

Characteristic infrared absorption: C=O structure: 1750 cm$^{-1}$. —CH=CH$_2$ structure: 1620 cm$^{-1}$.
NMR parameter (C$^{13}$, in CDCl$_3$):

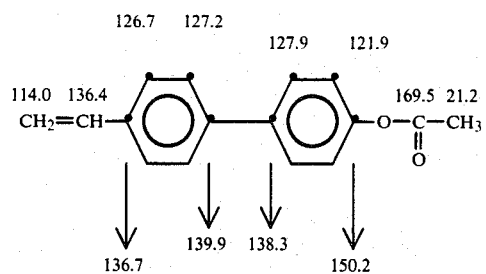

EXAMPLE 9

Production of 4-acetoxy-4'-acetylbiphenyl (1)
(Friedel-Crafts reaction)

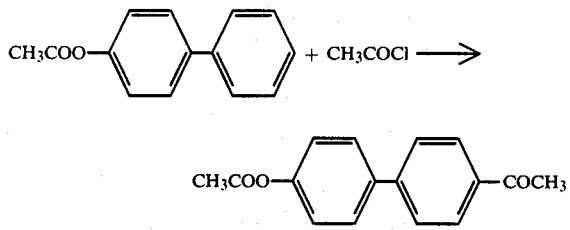

300 ml of CH$_2$Cl$_2$ and 78 g of AlCl$_3$ were charged in a three-necked flask provided with a calcium chloride tube, a condenser and a stirrer. 46 g of acetyl chloride was added thereto under stirring in a water bath.

After dissolution of AlCl$_3$ to obtain a homogeneous solution, 50 g of biphenyl acetate was added to the solution followed by stirring at room temperature for 24 hr to effect the reaction.

After completion of the reaction, the reaction mixture was poured onto ice/water containing hydrochloric acid. A CH$_2$Cl$_2$ layer was separated, washed with water and dried. Then, CH$_2$Cl$_2$ was removed and the residue was concentrated to obtain 56 g of a solid.

The solid was recrystallized from CCl$_4$ to obtain 51 g of 4-acetoxy-4'-acetylbiphenyl (1) of the following formula:

 (1)

Yield: 85%
Melting point: 124.5° to 126.0° C.

EXAMPLE 10

Production of 4-acetoxy-4'-acetylbiphenyl (1)
(Friedel-Crafts reaction)

The reaction was carried out using 2.1 g of biphenyl acetate, 1.8 g of acetyl chloride and 3.5 g of AlCl$_3$ at room temperature for 12 hr in the same manner as in Example 1 using various solvents. The results are shown in Table 4:

TABLE 4

| Solvent, 20 ml | Yield (%) |
|---|---|
| CHCl$_3$ | 70 |
| CS$_2$ | 32 |
| ⌬—NO$_2$ | 75 |
| CCl$_4$ | 50 |

When 20 ml of CHCl$_3$ was used as the solvent and 3.5 g of FeCl$_3$ was used as the catalyst, the yield was 43%

EXAMPLE 11

Production of 4-acetoxy-4'-acetylbiphenyl (1)
(Friedel-Crafts reaction)

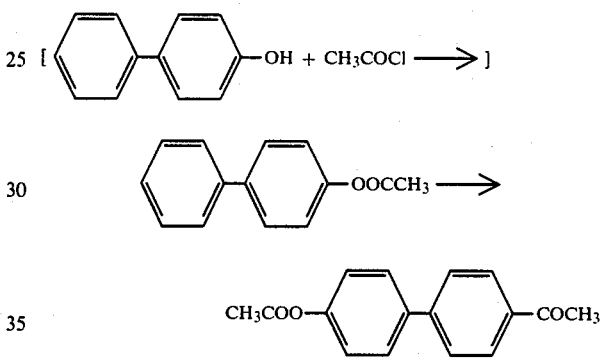

The reaction was carried out using 80 g (molar ratio: (1) of 4-hydroxybiphenyl, 110 g (molar ratio: 2.55) of acetyl chloride, 150 g (molar ratio: 2.47) of AlCl$_3$ and 550 ml of CH$_2$Cl$_2$ at room temperature in the same manner as in Example 1 except that biphenyl acetate was not separated out of the reaction system. The results are shown in Table 5.

TABLE 5

| Reaction time (hr) | Yield (%) |
|---|---|
| 0.5 | 96 |
| 1 | 90 |
| 24 | 82 |

When a mixture of 4-hydroxybiphenyl with acetyl chloride and AlCl$_3$ in a molar ratio of 1:1:1 was reacted for 1 hr, only 4-acetoxybiphenyl

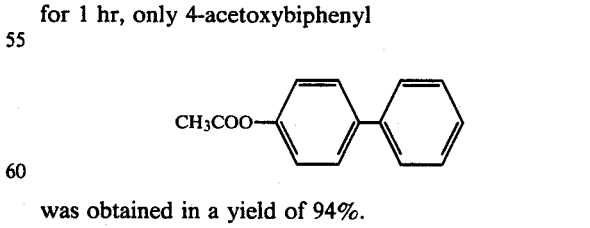

was obtained in a yield of 94%.

EXAMPLE 12

Production of 4-benzoyloxy-4'-benzoylbiphenyl
[compound (11)]

300 ml of CH$_2$Cl$_2$ and AlCl$_3$ were charged in a three-necked flask. Benzoyl chloride [compound of the general formula(VII)] was added thereto under stirring in a water bath. After the dissolution of AlCl₃ to form a homogeneous reaction solution, biphenyl acetate [compound of the general formula (VI)] was added to the solution followed by stirring at room temperature to 50° C. for 5 to 10 hr. The reaction mixture was poured onto ice/water containing hydrochloric acid. After separation of a CH₂Cl₂ layer followed by washing with water and drying, CH₂Cl₂ was removed and the residue was concentrated to obtain the compound (11). The molar ratio of benzoyl chloride to biphenyl acetate was 1:1.2 to 2.0. The amount of AlCl₃ used was 2 to 5 mol. The results are shown in Table 6.

When 1.2 mol of benzoyl chloride was used per mol of biphenyl acetate and the reaction was carried out at room temperature, the compound (25) was obtained as described above. However, when 2.0 mol of benzoyl chloride was used and the reaction was carried out at 40° C., an acyl exchange reaction occurred as shown below to obtain the compound (11):

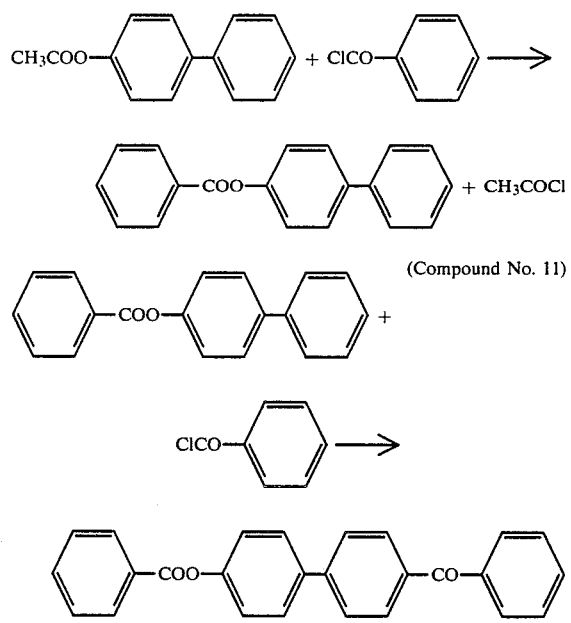

(Compound No. 11)

The acyl exchange reaction also occurred in the production of the compounds (20) and (21).

EXAMPLE 13

Compounds (12) to (25) were produced in the same manner as in Example 12 using various compounds of the general formule (VI) and (VII). The results are shown in Table 6.

The characteristic infrared absorption and NMR parameter of the resulting compounds (11) to (25) are shown in Table 7.

EXAMPLE 14

Production of 4-hydroxy-4′-benzoylbiphenyl [compound (31)]

4-Benzoyloxy-4′-benzoylbiphenyl [compound (11)] in Example 12 was added to an alkali-containing tetrahydrofuran followed by stirring at room temperature for several hours. After completion of the reaction, the tetrahydrofuran solution was concentrated to obtain 4-hydroxy-4′-benzoylbiphenyl [compound (31)]. The results are shown in Table 8.

EXAMPLE 15

The compounds (12) to (15) and (21) were hydroxylated with an alkali in the same manner as in Example 14. The results are shown in Table 8.

The characteristic infrared absorption and NMR parameter of the resulting new compounds (31) to (37) are shown in Table 9.

The compound (32) in Table 8 was formed by the direct hydrolysis without separation of the compound (33) from the reaction system as follows:

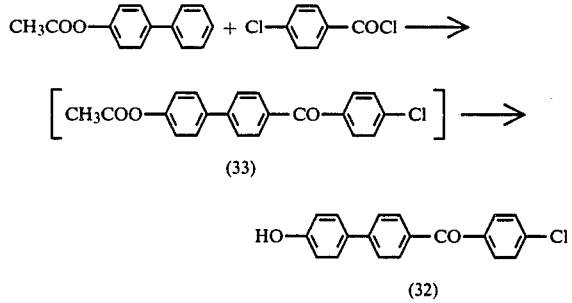

TABLE 6

RCOO—⟨⟩—⟨⟩—CO—R'

| Compound No. | Compound of general formula (VI) | Compound of general formula (VII) | Product of general formula (VIII) | M.P. (°C.) | Yield (%) | Elementary Analysis (%) Found | Elementary Analysis (%) Calcd. |
|---|---|---|---|---|---|---|---|
| (11) | CH₃COO—⟨⟩—⟨⟩— | ⟨⟩—COCl | CH₃COO—⟨⟩—⟨⟩—CO—⟨⟩—OOC—⟨⟩ | 168.8~171.5 | 52 | C: 82.52 H: 4.79 | C: 82.57 H: 4.68 |
| (12) | CH₃COO—⟨⟩—⟨⟩— | CH₂—COOCH₃ / CH₂—COCl | CH₃COO—⟨⟩—⟨⟩—COCH₂CH₂COOH | 170~171 | 61.3 | C: 69.22 H: 5.16 | C: 69.67 H: 5.20 |
| (13) | CH₃COO—⟨⟩—⟨⟩— | CH₃(CH₂)₈COCl | CH₃COO—⟨⟩—⟨⟩—CO(CH₂)₈CH₃ | 114~118 | 58 | C: 78.65 H: 8.25 | C: 78.92 H: 8.56 |
| (14) | CH₃COO—⟨⟩—⟨⟩— | ClCO—⟨⟩—COOCH₃ | CH₃COO—⟨⟩—⟨⟩—CO—⟨⟩—COOCH₃ | 214~215 | 66 | C: 73.79 H: 4.85 | C: 74.18 H: 4.70 |
| (15) | CH₃COO—⟨⟩—⟨⟩— | COOC₂H₅ / (CH₂)₄ / COCl | CH₃COO—⟨⟩—⟨⟩—CO(CH₂)₄COOC₂H₅ | 131~133 | 74 | C: 71.72 H: 6.57 | C: 71.81 H: 6.90 |
| (16) | CH₃COO—⟨⟩—⟨⟩— | ClCH₂COCl | CH₃COO—⟨⟩—⟨⟩—COCH₂Cl | 138~139 | 95 | C: 66.56 H: 4.54 | C: 66.33 H: 4.42 |
| (17) | CH₃COO—⟨⟩—⟨⟩— | CH₃COO—⟨Br⟩—COCl | CH₃COO—⟨⟩—⟨⟩—CO—⟨Br⟩—OOCCH₃ | 158.5~160 | 30 | C: 60.94 H: 3.78 | C: 60.73 H: 3.63 |
| (18) | CH₃COO—⟨⟩—⟨⟩— | CH₂=C(CH₃)COCl | CH₃COO—⟨⟩—⟨⟩—COC(CH₃)=CH₂ | 66~70 | 20 | C: 77.12 H: 5.75 | C: 77.32 H: 5.86 |
| (19) | CH₃COO—⟨⟩—⟨⟩— | naphthol-COCl (OH) | CH₃COO—⟨⟩—⟨⟩—CO—naphthol-OH | 173~174 | 15 | C: 78.52 H: 4.74 | C: 78.71 H: 4.86 |
| (20) | CH₃COO—⟨⟩—⟨⟩— | NO₂—⟨⟩—COCl | NO₂—⟨⟩—CO₂—⟨⟩—⟨⟩—CO—⟨⟩—NO₂ | 195.5~197 | 30 | C: 66.67 H: 3.44 N: 5.98 | C: 66.62 H: 3.27 N: 6.03 |

TABLE 6-continued
General structure: RCOO—⟨phenyl⟩—⟨phenyl⟩—CO—R'
| Compound No. | Compound of general formula (VI) | Compound of general formula (VII) | Product of general formula (VIII) | M.P. (°C.) | Yield (%) | Elementary Analysis (%) Found | Elementary Analysis (%) Calcd. |
|---|---|---|---|---|---|---|---|
| (21) |  |  |  | 187~189 | 40 | C: 72.86  H: 4.48 | C: 72.34  H: 4.25 |
| (22) |  | ClCO.COCl |  | 170 (decomp.) | 35 | C: 75.30  H: 4.63 | C: 74.86  H: 4.43 |
| (23) |  | ClCO(CH$_2$)$_4$COCl |  | >230 (decomp.) | 80 | C: 76.39  H: 5.66 | C: 76.17  H: 5.30 |
| (24) |  |  |  | 124.5~126.5 | 53 | C: 80.68  H: 5.30 | C: 80.66  H: 5.57 |
| (25) |  |  |  | 124.0~125 | 20 | C: 79.73  H: 5.10 | C: 79.52  H: 5.05 |

TABLE 7

| Compound No. | Characteristic infrared absorption (cm$^{-1}$) | NMR parameter |
|---|---|---|
| (11) | COO Structure 1720<br>CO Structure 1640 | Ph-C(=O)(165.0)-O-Ph-Ph-C(=O)(196.0)-Ph<br>122.3(d), 126.9(d), 128.3(d), 128.6(d), 129.9(d), 130.2(d), 130.7(d), 132.3(d), 133.7(d), 136.4(s), 137.7(s), 137.8(s), 144.3(s), 151.2(s), 165.0(s) |
| (12) | COO Structure 1750<br>CO Structure 1670<br>COOH Structure 1700 | $CH_3$(21.4)-C(170.2)(=O)-O-Ph-Ph-C(199.0)(=O)-$CH_2$(28.5)-$CH_2$(33.8)-C(174.8)(=O)-OH<br>123.1(d), 127.5(d), 128.7(d), 129.2(d), 135.7(s), 137.0(s), 144.4(s), 151.2(s) |
| (13) | COO Structure 1750<br>CO Structure 1670 | $CH_3$(21.1)-C(169.3)(=O)-O-Ph-Ph-C(199.9)(=O)-$(CH_2)_8$-$CH_3$(14.1)<br>Ar. 122.1(d), 127.1(d), 128.2(d), 128.6(d), 135.8(s), 137.6(s), 144.5(s), 150.8(s), Alk. 22.7, 24.5, 25.0, 29.3, 29.5, 31.9, 34.4, 38.7 |
| (14) | COO Structure 1750<br>1720<br>CO Structure 1640 | $CH_3$(21.1)-C(169.1)(=O)-O-Ph-Ph-C(195.3)(=O)-Ph-C(166.3)(=O)-O-$CH_3$(52.4)<br>Ar. 122.2(d), 127.1(d), 128.4(d), 129.7(d), 130.7(d), 133.4(d), 139.5(s), 137.6(s), 141.7(s), 144.9(s), 151.2(s) |
| (15) | COO Structure 1750<br>1720<br>CO Structure 1670 | $CH_3$(21.1)-C(169.3)(=O)-O-Ph-Ph-C(199.3)(=O)-$(CH_2)_4$-C(173.4)(=O)-O-$CH_2$(60.3)-$CH_3$(14.3)<br>Ar. 122.1(d), 127.1(d), 128.2(d), 128.6(d), 135.7(s), 137.5(s), 144.6(s), 150.8(s), Alk. 23.7, 24.7, 34.2, 38.2 |
| (16) | COO Structure 1750<br>CO structure 1690 | $CH_3$(20.4)-C(168.6)(=O)-O-Ph-Ph-C(190.8)(=O)-$CH_2$(46.4)-Cl<br>Ar. 122.0(d), 126.6(d), 127.7(d), 128.8(d), 133.1(s), 136.0(d), 144.2(s), 150.7(s) |
| (17) | COO Structure 1770<br>1750<br>CO Structure 1650 | $CH_3$-C(169.4)(168.1)(=O)(21.3)(21.0)-O-Ph-Ph-C(195.4)(=O)-Ph(Br)-O-C(168.1)(169.4)(=O)(21.0)(21.3)-$CH_3$<br>122.2(d), 123.8(d), 127.2(d), 128.5(d), 130.3(d), 130.7(d), 135.0(d), 116.7(s), 135.6(s), 136.9(s), 137.6(s), 144.8(s), 150.9(s), 151.5(s) |
| (18) | COO Structure 1750<br>CO Structure 1640 | $CH_3$(21.1)-C(169.3)(=O)-O-Ph-Ph-C(197.7)(=O)-C(=$CH_2$(127.3))-$CH_3$(18.7)<br>122.1(d), 126.8(d), 128.2(d), 130.0(d), 128.5(s), 136.4(s), 137.7(s), 143.8(s), 150.8(s) |
| (19) | COO Structure 1750<br>CO Structure 1640 | $CH_3$(21.1)-C(169.2)(=O)-O(151.1)-Ph-Ph-C(201.0)(=O)-Naphthyl(OH, 157.4)<br>112.5(d), 122.2(d), 124.1(d), 126.3(d), 127.1(d), 128.4(d), 129.6(d), 129.8(d), 130.3(d), 136.4(d), 121.4(s), 126.9(s), 136.9(s), 137.5(s), 138.0(s), 144.4(s) |

TABLE 7-continued

| Compound No. | Characteristic infrared absorption (cm$^{-1}$) | NMR parameter |
|---|---|---|
| (20) | COO Structure 1730<br>CO Structure 1650 | NO$_2$–⟨Ph⟩–C(167.9)(=O)–O–⟨Ph⟩–⟨Ph⟩–C(194.3)(=O)–⟨Ph⟩–NO$_2$<br>122.2(d), 123.6(d), 123.9(d), 127.5(d), 128.7(d), 130.7(d), 130.9(d),<br>131.4(d), 134.8(s), 135.3(s), 138.0(s), 143.1(s), 145.1(s), 150.1(s), 150.9(s), 151.1(s) |
| (21) | COO Structure 1730, 1750<br>CO Structure 1640 | (21.2) CH$_3$–C(=O)–O–⟨Ph⟩–C(=O)–O–⟨Ph⟩–⟨Ph⟩–C(195.1)(=O)–⟨Ph⟩–O–C(=O)–CH$_3$ (21.2)<br>—COO—: 160.4(s), 168.7(s), 169.4(s)<br>Ar. 121.8(d), 122.1(d), 122.2(d), 127.0(d),<br>128.5(d), 130.7(d), 131.7(d), 131.9(d),<br>126.7(s), 135.4(s), 136.3(s), 144.4(s),<br>150.9(s), 154.2(s), 155.2(s) |
| (22) | COO Structure 1750<br>CO Structure 1720 | 21.3  169.5                    198.7<br>CH$_3$–C(=O)–O–⟨Ph⟩–⟨Ph⟩–C(=O)–C(=O)–⟨Ph⟩–⟨Ph⟩–O–C(=O)–CH$_3$<br>       151.0<br>Ar. 122.3(d), 127.3(d), 128.5(d), 130.9(d),<br>137.5(s), 144.2(s), 144.8(s) |
| (23) | COO Structure 1750<br>CO Structure 1680 | 21.1 169.2          199.4 38.6 24.3<br>CH$_3$–C(=O)–O–⟨Ph⟩–⟨Ph⟩–C(=O)–CH$_2$–CH$_2$<br>                              CH$_2$–CH$_2$<br>                    O=C–⟨Ph⟩–⟨Ph⟩–O–C(=O)–CH$_3$<br>Ar. 122.2(d), 127.3(d), 128.3(d), 128.8(d)<br>136.1(s), 137.8(s), 144.8(s) |
| (24) | COO Structure 1740<br>CO Structure 1640 | 127.5 165.7         122.2<br>CH$_2$=C–C(=O)–O–⟨Ph⟩–⟨Ph⟩–C(196.2)(=O)–⟨Ph⟩<br>    CH$_3$  151.0<br>Ar. 126.8(d), 128.3(d), 130.0(d), 130.7(d), 132.4(d),<br>135.7(s), 137.5(s), 137.7(s), 144.3(s), |
| (25) | COO Structure 1750<br>CO Structure 1640 | 21.1 169.3              169.1<br>CH$_3$–CO–⟨Ph⟩–⟨Ph⟩–CO–⟨Ph⟩<br>     O  150.7<br>Ar. 122.1(d), 126.8(d), 128.3(d), 129.9(d), 130.6(d), 132.3(d),<br>136.9(s), 137.6(s), 144.2(s) |

TABLE 8

| Compound No. | Starting compound No. | Product of general formula (IV) | M.P. (°C.) | Yield (%) | Elementary Analysis Calcd. | Elementary Analysis Found |
|---|---|---|---|---|---|---|
| (31) | (11) | HO—⟨⟩—⟨⟩—CO—⟨⟩ | 194.0~195.5 | 94 | C: 83.19 H: 5.14 | C: 83.00 H: 5.13 |
| (32) | — | HO—⟨⟩—⟨⟩—CO—⟨⟩—Cl | 196~197 | 74 | C: 73.90 H: 4.21 | C: 73.91 H: 4.21 |
| (33) | (12) | HO—⟨⟩—⟨⟩—CO—$CH_2$—$CH_2$—COOH | 228~230 | 86 | C: 71.10 H: 5.22 | C: 70.97 H: 5.13 |
| (34) | (13) | HO—⟨⟩—⟨⟩—CO—$(CH_2)_8$—$CH_3$ | 138~140 | 73 | C: 81.44 H: 8.70 | C: 81.53 H: 8.79 |
| (35) | (14) | HO—⟨⟩—⟨⟩—CO—⟨⟩—COOH | >250 | 62 | C: 75.46 H: 4.43 | C: 75.32 H: 4.21 |
| (36) | (15) | HO—⟨⟩—⟨⟩—$CO(CH_2)_4COOH$ | 107~127 | 71 | C: 72.47 H: 6.08 | C: 72.25 H: 6.02 |
| (37) | (21) | HO—⟨⟩—⟨⟩—CO—⟨⟩—OH | 230~232 | 65 | C: 78.61 H: 4.86 | C: 78.85 H: 4.91 |

TABLE 9

| Compound No. | Characteristic infrared absorption (cm$^{-1}$) | NMR Parameter |
|---|---|---|
| (31) | HO Structure 3400 | 158.1, 116.0, 195.2 (HO—⟨⟩—⟨⟩—CO—⟨⟩) |
| | CO Structure 1640 | Ar: 125.8(d), 128.2(d), 128.5(d), 129.5(d), 130.5(d), 132.3(d), 134.6(d), 137.4(s), 144.3(s) |
| (32) | HO Structure 3500~3600 | 158.2, 116.2, 194.4 (HO—⟨⟩—⟨⟩—CO—⟨⟩—Cl) |
| | CO Structure 1640 | Ar: 126.0(d), 128.4(d), 128.8(d), 130.6(d), 131.5(d), 129.7(s), 134.5(s), 136.1(s), 137.7(s) |
| (33) | HO Structure 3250~3300 | 158.3, 116.6, 199.0, 174.9 (HO—⟨⟩—⟨⟩—CO—$CH_2$—$CH_2$—C—OH; 28.6, 33.6) |
| | CO Structure 1680 COO Structure 1710 | Ar: 126.5(d), 128.8(d), 129.2(d), 130.2(s), 134.8(s), 145.2(s) |
| (34) | HO Structure 3350 | 150.8, 116.1, 199.8, 14.0 (HO—⟨⟩—⟨⟩—CO—$(CH_2)_8$—$CH_3$) |
| | CO Structure 1670 | Ar: 126.0(d), 128.2(d), 128.7(d), 129.8(s), 134.7(s), 144.5(s), Alk: 22.2, 24.2, 28.8, 29.0, 31.4, 31.4, 33.9 |

TABLE 9-continued

| Compound No. | Characteristic infrated absorption (cm⁻¹) | | NMR Parameter |
|---|---|---|---|
| (35) | HO Structure | 3400 | 157.8 ... structure shown ... HO—⬡—⬡—C(=O)—⬡—C(=O)—OH with values 115.9, 172.5, 167.4 |
| | CO Structure | 1640 | Ar: 125.7(d), 127.9(d), 129.0(d), 130.1(d), |
| | COO Structure | 1700 | 129.6(s), 132.5(s), 134.1(s), 136.1(s) |
| (36) | HO Structure | 3400 | 158.0 ... structure: HO—⬡—⬡—C(=O)—(CH₂)₄—C(=O)—OH with 116.1, 199.6, 173.0 |
| | CO Structure | 1670 | Ar: 126.0(d), 128.2(d), 128.6(d), 129.8(s), 134.7(s), 144.7(s) |
| | COO Structure | 1710 | Alk: 23.5, 24.3, 33.7, 59.9 |
| (37) | HO Structure | 3250~3450 | 116.0, 115.2, structure: HO—⬡—⬡—C(=O)—⬡—OH with 193.8, 157.1, 161.9 |
| | CO Structure | 1630 | 125.6(d), 128.1(d), 130.0(d), 132.3(d) 128.1(s), 129.6(s), 135.7(s), 143.5(s) |

EXAMPLE 16

Production of 2-acetoxy-4'-acetylbiphenyl

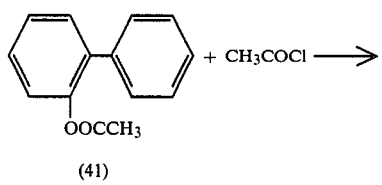

(41) + CH₃COCl ⟶

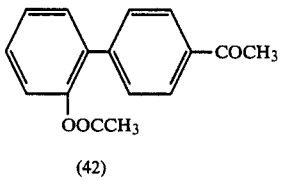

(42)

380 ml of methylene chloride was charged in a flask provided with a reflux condenser, a stirrer and a calcium chloride drying tube. 176 g of AlCl₃ and 78 g of acetyl chloride were added thereto under cooling in an ice bath. After dissolution of aluminum chloride, 70 g of o-acetoxybiphenyl [compound (41)] was added to the solution and the mixture was reacted at room temperature for 20 hr.

The reaction mixture was poured onto a hydrochloric acid-containing ice/water. The resulting methylene chloride layer was separated, washed with water, dried and concentrated. A solid thus obtained was recrystallized from methanol to obtain 53.7 g of 2-acetoxy-4'-acetylbiphenyl [compound (42)] as white crystals. Yield: 64%. M.P. 116°–117° C.

2-Acetoxybiphenyl [compound (41)] was obtained by dissolving 59 g of 2-hydroxybiphenyl in 40 ml of acetic anhydride, adding a small amount of concentrated sulfuric acid, heating them under reflux for 20 min, pouring the reaction mixture in water, filtering the formed crystals and recrystallizing the same from methanol to obtain the compound (41) in a yield of 97%. M.P. 63°–64° C.

EXAMPLE 17

Production of 4-hydroxy-4'-acetylbiphenyl (C)

25 g of 4-acetoxy-4'-acetylbiphenyl obtained in Example 9 was added to an alkali-containing tetrahydrofuran followed by stirring at room temperature for several hours.

After completion of the reaction, the tetrahydrofuran solution was concentrated to obtain 19 g of 4-hydroxy-4'-acetylbiphenyl:

HO—⬡—⬡—COCH₃

M.P. 207.5°–208.5° C. Yield: 91%.

EXAMPLES 18 TO 24

4-Acyloxy-4'-acylbiphenyls were hydrolyzed in the same manner as in Example 17. The results are shown in Table 10.

TABLE 10

| Example No. | Compound of general formula (VIII) | Alkali | Solvent | Reaction time (hr) | Compound of general formula (IX) | Yield (%) | M.P. (°C.) |
|---|---|---|---|---|---|---|---|
| 18 | C₆H₅-COO-C₆H₄-C₆H₄-CO-C₆H₄-Cl | NaOH | Tetrahydrofuran | 2 | HO-C₆H₄-C₆H₄-CO-C₆H₄-Cl | 74 | 196~197 |
| 19 | CH₃COO-C₆H₄-C₆H₄-COCH₂CH₂COOH | NaOH | " | 2 | HO-C₆H₄-C₆H₄-COCH₂CH₂COOH | 86 | 228~230 |
| 20 | CH₃COO-C₆H₄-C₆H₄-COO-C₆H₄-CO-C₆H₄-OOCCH₃ | NaOH | " | 2 | HO-C₆H₄-C₆H₄-CO-C₆H₄-OH | 65 | 230~232 |
| 21 | CH₃COO-C₆H₄-C₆H₄-CO(CH₂)₈CH₃ | NaOH | " | 2 | HO-C₆H₄-C₆H₄-CO(CH₂)₈CH₃ | 73 | 138~140 |
| 22 | CH₃COO-C₆H₄-C₆H₄-CO-C₆H₄-COOCH₃ | NaOH | " | 2 | HO-C₆H₄-C₆H₄-CO-C₆H₄-COOH | 62 | >250 |
| 23 | CH₃COO-C₆H₄-C₆H₄-CO-(CH₂)₄COOC₂H₅ | NaOH | " | 2 | HO-C₆H₄-C₆H₄-CO(CH₂)₄CCOH | 71 | 107~127 |
| 24 | C₆H₅-COO-C₆H₄-C₆H₄-CO-C₆H₅ | NaOH | " | 2 | HO-C₆H₄-C₆H₄-CO-C₆H₅ | 94 | 193.5~194.5 |

EXAMPLE 25

Production of 4-hydroxy-4'-(1-hydroxyisopropyl)biphenyl (51)

5 g of dry magnesium and 80 ml of ether were charged in a three-necked flask provided with a reflux condenser, a stirrer and a calcium chloride drying tube, and cooled to 0° C. 15 ml of methyl iodide was added thereto under stirring and the reaction was carried out for 3 hr. A solution of 10 g of 4-acetoxy-4'-acetylbiphenyl (1) in 100 ml of tetrahydrofuran was added thereto and the reaction was carried out under stirring at room temperature for 1 hr.

The reaction solution was poured onto a hydrochloric acid-containing ice/water and crystals thus formed were separated.

The resulting yellowish white precipitate was recrystallized from benzene to obtain 7.5 g of 4-hydroxy-4'-(1-hydroxyisopropyl)biphenyl (51) in the form of crystals:

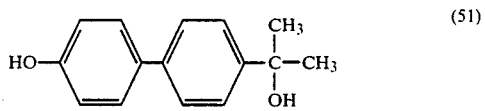

Yield: 83.5%
Melting point: 187.5° to 189° C.

| Elementary analysis: | C (%) | H (%) |
|---|---|---|
| calculated: | 78.92 | 7.06 |
| found: | 78.73 | 6.98 |

Characteristic infrared absorption: OH structure: 3350 cm$^{-1}$.

NMR parameter (C$^{13}$, in DMSO):

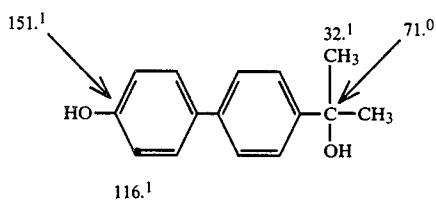

125.3 (C), 125.6 (D), 127.8 (D), 131.3 (S), 138.1 (S), 148.8 (S).

EXAMPLE 26

Production of 4-hydroxy-4'-isopropenylbiphenyl (52)

20 ml of dimethyl sulfoxide and 10 g of 4-hydroxy-4'-(2-hydroxy-2-propyl)biphenyl (51) obtained in Example 1 were charged in a flask provided with a condenser and a stirrer to obtain a homogeneous solution. 2.5 g of zinc chloride was added to the solution and the mixture was heated to 180° C. to dissolve zinc chloride, thereby obtaining a yellow solution.

2.5 g of trichloriacetic acid was added to the solution under stirring and then the stirring was continued at 180° C. for 3 min.

The reaction solution was cooled to room temperature and poured into water and crystals thus formed were separated.

The crystals were dissolved in acetone and extracted with hexane. After concentration to remove hexane, the resulting crystals were recrystallized from benzene to obtain 5.3 g of white crystals.

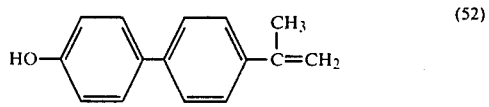

Yield: 57.5%
Melting point: 199° to 201° C.

| Elementary analysis: | C (%) | H (%) |
|---|---|---|
| calculated: | 85.68 | 6.71 |
| found: | 85.32 | 6.57 |

Characteristic infrared absorption: OH structure: 3400 cm$^{-1}$. C=C structure: 1620 cm$^{-1}$.

NMR parameter (C$^{13}$, in DMSO):

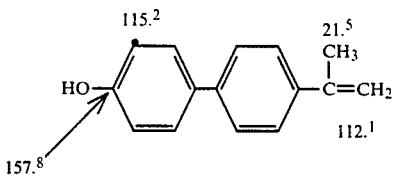

125.8 (D), 127.6 (D), 130.4 (S), 138.3 (S), 139.4 (S), 142.1 (S).

EXAMPLE 27

Production of 4-acetoxy-4'-isopropenylbiphenyl (53)

10 ml of acetic anhydride was charged in a flask provided with a reflux condenser and a stirrer. Then, 1 g of 4-hydroxy-4'-isopropenylbiphenyl obtained in Example 2 was added thereto and the mixture was stirred at 80° C. for 1 hr to effect the reaction. The reaction solution was poured into water and the resulting crystals were separated and recrystallized from methanol to obtain 0.72 g of 4-acetoxy-4'-isopropenylbiphenyl (53) in the form of white crystals.

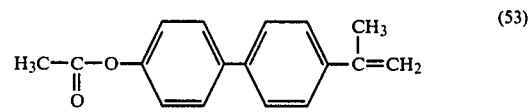

Yield: 60%
Melting point: 131.0° to 131.5° C.

| Elementary analysis: | C (%) | H (%) |
|---|---|---|
| calculated: | 80.93 | 6.39 |
| found: | 80.75 | 6.23 |

Characteristic infrared absorption: C=O structure: 1750 cm$^{-1}$ C=C structure: 1620 cm$^{-1}$ NMR parameter (C$^{13}$, in DMSO):

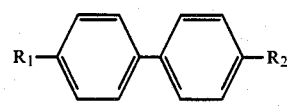

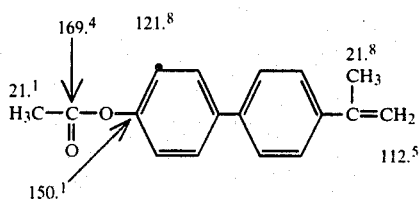

125.9 (D), 126.8 (D), 127.9 (D), 138.4 (S), 139.7 (S), 142.6 (S).

I claim:

1. A new biphenyl compound of the following general formula:

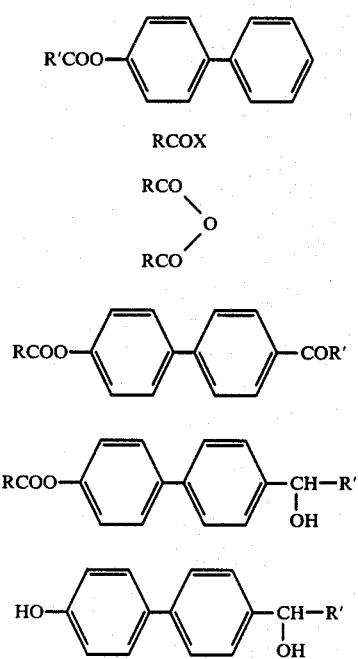

wherein $R_1$ is an acetoxy group or an hydroxyl group, and $R_2$ is a 1-hydroxyethyl or vinyl group.

2. A process for producing a biphenyl compound which comprises reacting a 4-acyloxybiphenyl of the general formula (P) with an acyl halide of the general formula (VII) or an acid anhydride of the general formula (R) in the presence of a Friedel-Crafts catalyst in an inert solvent to form a 4-acyloxy-4'-acylbiphenyl of the general formula (I), reducing the compound (I) to form a 4-acyloxy-4'-(1-hydroxyalkyl)biphenyl of the general formula (II) or a 4-hydroxy-4'-(1-hydroxyalkyl)biphenyl of the general formula (IV), acylating the compound (IV) to obtain the above-mentioned compound (II) and simultaneously dehydrating the compound (IV) to form a 4-hydroxy-4'-(1-alkenyl)biphenyl of the general formula (V) and acylating the compound (V) to form a 4-acyloxy-4'-(1-alkenyl)biphenyl of the general formula (III):

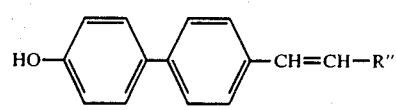

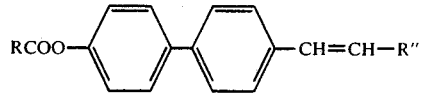

wherein R and R' are each a lower alkyl and R" is a lower alkyl group having a carbon number smaller than that of R' by one, or a hydrogen atom.

3. A process for producing a biphenyl compound according to claim 2, wherein the Friedel-Crafts catalyst is selected from the group consisting of $AlCl_3$, $FeCl_3$, $TiCl_4$, $SnCl_4$, $ZnCl_2$ and $BF_3O(C_2H_5)_2$.

4. A process for producing a biphenyl compound according to claim 2, wherein the inert solvent is a halogenated lower aliphatic saturated hydrocarbon, $CS_2$ or nitrobenzene.

5. A process for producing a biphenyl compound according to claim 2, wherein the compound (I) is reduced with hydrogen in the presence of a metal catalyst or with a metal hydride.

6. A process for producing a biphenyl compound according to claim 5, wherein the metal catalyst is a platinum or transition metal catalyst.

7. A process for producing a biphenyl compound according to claim 2, wherein the dehydration is effected by heating in the presence of zinc chloride and trichloroacetic acid.

8. A process for producing biphenyl compound of the following general formula (VIII) which comprises reacting a 2- or 4-acyloxybiphenyl compound of the following general formula (VI) with an acyl halide of the general formula (VII) or an acid anhydride of the general formula (R) in the presence of a Friedel-Crafts catalyst in an inert solvent:

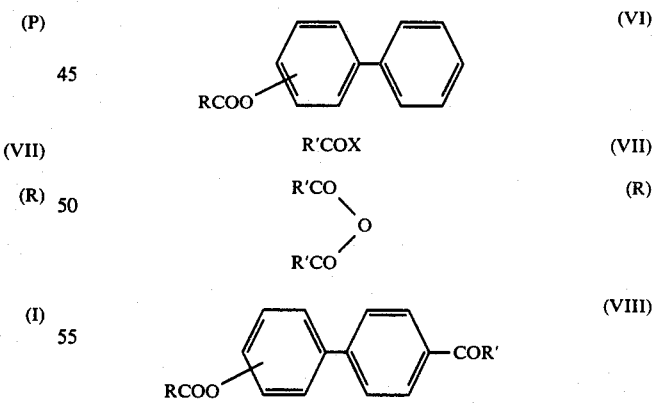

wherein R is a substituted or unsubstituted alkyl group, a substituted or unsubstituted alkenyl group or a substituted or unsubstituted aryl group, R' is a substituted or unsubstituted alkyl group, a substituted or unsubstituted alkenyl group, a substituted or unsubstituted aryl group or a carbonyl halide group and X is a halogen atom.

9. A process for producing a biphenyl compound of the following general formula (IX) which comprises reacting a 2- or 4-acyloxybiphenyl compound of the following general formula (VI) with an acyl halide of the general formula (VII) or an acid anhydride in the presence of a Friedel-Crafts catalyst in an inert solvent and then hydrolyzing the obtained 2- or 4-acyloxy-substituted 4'-acylbiphenyl compound of the general formula (VIII):

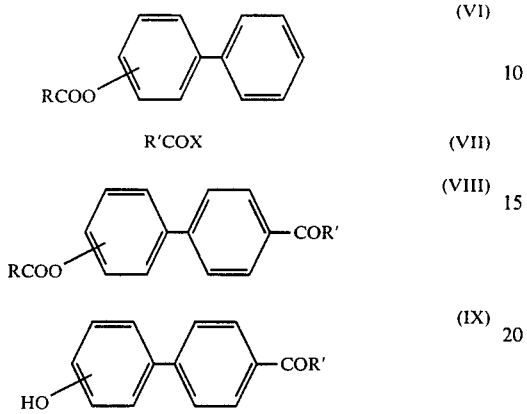

wherein R is a substituted or unsubstituted alkyl group, a substituted or unsubstituted alkenyl group or a substituted or unsubstituted aryl group, R' is a substituted or unsubstituted alkyl group, a substituted or unsubstituted alkenyl group, a substituted or unsubstituted aryl group or a carbonyl halide group and X is a halogen atom.

10. A process for producing a biphenyl compound according to claim 8, wherein the Friedel-Crafts catalyst is selected from the group consisting of AlCl$_3$, FeCl$_3$, TiCl$_4$, SnCl$_4$, ZnCl$_2$ and BF$_3$O(C$_2$H$_5$)$_2$.

11. A process for producing a biphenyl compound according to claim 8, wherein the inert solvent is a halogenated lower aliphatic saturated hydrocarbon, CS$_2$ or nitrobenzene.

12. A process for producing a biphenyl compound according to claim 9, wherein the hydrolysis is effected in the presence of an alkali.

13. A new biphenyl compound of the following general formula:

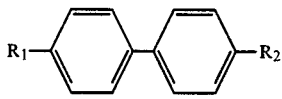

wherein R$_1$ is hydroxyl or acetoxy and R$_2$ is isopropenyl.

14. A process for producing a biphenyl compound which comprises reacting a 2- or 4-acyloxybiphenyl compound of the following general formula (VI) with an acyl halide of the general formula (VII) or an acid anhydride of the general formula (R) in the presence of a Friedel-Crafts catalyst in an inert solvent, subjecting the resulting 2- or 4-acyloxy-4'-acylbiphenyl compound of the general formula (VIII) to Grignards reaction with magnesium and a methyl halide in ether to form a 2- or 4-hydroxy-4'-(1-hydroxy-1-methylalkyl)biphenyl of the general formula (X), dehydrating the compound (X) to form a 4-hydroxy-4'-(1-methylalkenyl)biphenyl of the general formula (XI) and acylating the compound (XI) to form a 4-acyloxy-4'-(1-methylalkenyl)biphenyl of the general formula (XII):

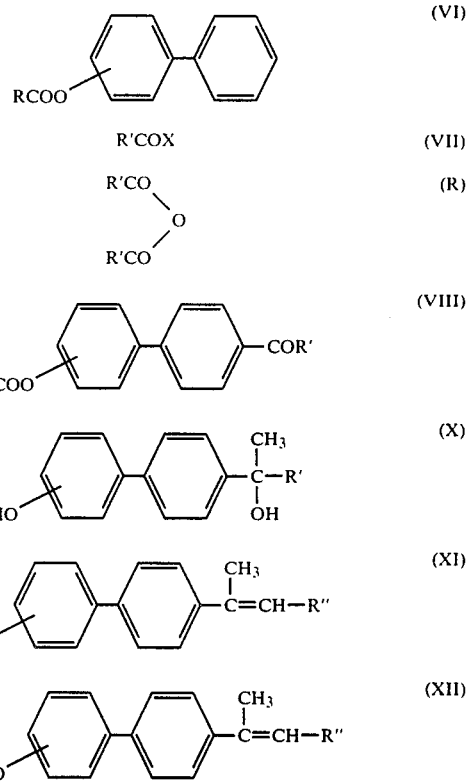

wherein R and R' each is a substituted or unsubstituted alkyl group, R" is a substituted or unsubstituted alkyl group having a carbon number smaller than that of R' by one or a hydrogen atom and X is a halogen atom.

15. A process for producing a biphenyl compound according to claim 14, wherein the Friedel-Crafts catalyst is selected from the group consisting of AlCl$_3$, FeCl$_5$, TiCl$_4$, SnCl$_4$, ZnCl$_2$ and BF$_3$O(C$_2$H$_5$)$_2$.

16. A process for producing a biphenyl compound according to claim 14, wherein the inert solvent is a halogenated lower aliphatic saturated hydrocarbon, CS$_2$ or nitrobenzene.

17. A process for producing a biphenyl compound according to claim 14, wherein the dehydration is effected with zinc chloride and trichloroacetic acid.

18. A process for producing a biphenyl compound according to claim 9, wherein the Friedel-Crafts catalyst is selected from the group consisting of AlCl$_3$, FeCl$_3$, TiCl$_4$, SnCl$_4$, ZnCl$_2$ and BF$_3$O(C$_2$H$_5$)$_2$.

19. A process for producing a biphenyl compound according to claim 9, wherein the inert solvent is halogenated lower aliphatic saturated hydrocarbon, CS$_2$ or nitrobenzene.

20. A new 4-acyloxy-4'-acylbiphenyl compound of the following general formula:

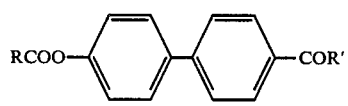

wherein when R is a phenyl group R' is a phenyl group; when R is a methyl group R' is a 2-carboxylethyl group, n-nonyl group, p-methoxycarbonylphenyl group, 4-ethoxycarbonyl-n-butyl group, chloromethyl group, p-acetoxy-m-bromophenyl group, isopropenyl group, 3-hydroxy-2-naphthyl group, 4'-acetoxybiphenyl-4-carbonyl group, 4-(4'-acetoxybiphenyl-4-carbonyl)-n-butyl group or phenyl group; when R is a p-nitrophenyl group R' is a p-nitrophenyl group; when R is a p-acetoxyphenyl group R' is a p-acetoxyphenyl group; and when R is an isopropenyl group R' is a phenyl group.

21. A new 4-hydroxy-4'acylbiphenyl compound of the following general formula:

wherein R' is a phenyl group, p-chlorophenyl group, 2-carboxyethyl group, n-nonyl group, p-carboxyphenyl group, 4-carboxy-n-butyl group or p-hydroxyphenyl group.

* * * * *